United States Patent [19]

Sieffert

[11] Patent Number: 5,236,358
[45] Date of Patent: Aug. 17, 1993

[54] DENTAL ULTRASONIC CALCULUS REMOVAL APPARATUS AND METHOD

[76] Inventor: William J. Sieffert, P.O. Box 416, Round Top Rd., Royston Shores, Chestertown, Md. 21620

[21] Appl. No.: 873,788

[22] Filed: Apr. 27, 1992

[51] Int. Cl.⁵ .................. A61C 1/07; A61C 3/03; A61C 3/08; A61C 5/02
[52] U.S. Cl. ................................ 433/119; 433/102
[58] Field of Search .............. 423/118, 119, 102, 81

[56] References Cited

U.S. PATENT DOCUMENTS

| | | | |
|---|---|---|---|
| 1,366,877 | 1/1921 | Craig | 433/102 X |
| 3,956,826 | 1/1976 | Perdreaux, Jr. | 32/58 |
| 3,972,123 | 8/1970 | Black | 32/58 |
| 4,174,571 | 11/1979 | Gallant | 433/216 |
| 4,229,168 | 10/1980 | Scholz, Jr. | 433/102 X |
| 4,295,827 | 10/1981 | Martin et al. | 433/119 X |
| 4,370,131 | 1/1983 | Banko | 433/119 X |
| 4,457,710 | 7/1984 | McSpadden | 433/81 |
| 4,492,574 | 1/1985 | Warrin et al. | 433/81 |
| 4,505,676 | 3/1985 | Gonser | 433/119 |
| 4,674,979 | 6/1987 | Jacklich | 433/102 |
| 4,731,019 | 3/1988 | Martin | 433/119 |
| 4,911,639 | 3/1990 | Jacklich | 433/119 X |
| 4,971,556 | 11/1990 | Ritano | 433/102 |

Primary Examiner—Gene Mancene
Assistant Examiner—Nicholas D. Lucchesi
Attorney, Agent, or Firm—Paul A. Fattibene; Arthur T. Fattibene

[57] ABSTRACT

An ultrasonic dental handpiece having a thin, flexible, elongated abrasive tool attached thereto for removing calculus deposits from the surface of teeth. A thin, flexible abrasive tool having a specifically selected diameter is used in conjunction with an ultrasonic handpiece for the purpose of removing calculus from deep within a periodontal pocket without traumatizing the surrounding tissue and bone. The use of a diamond coated abrasive tool aids in tactually detecting fine calculus deposits deep below the gum line. An annular aperture surrounding the circumference of the abrasive tool is used to provide a fluid spray for washing away loosened calculus. The ease and efficiency of calculus removal is greatly enhanced.

4 Claims, 2 Drawing Sheets

DENTAL ULTRASONIC CALCULUS REMOVAL APPARATUS AND METHOD

FIELD OF THE INVENTION

The present invention relates to ultrasonic teeth cleaning, and more specifically to the removal of calculus from the surface of a tooth in the periodontal pocket.

BACKGROUND OF THE INVENTION

It is important to preventive dentistry and healthy teeth that teeth be kept clean. Over time, various deposits can form on teeth. These deposits can form on the surface of a tooth below the gum line or in the periodontal pocket. Such deposits can take the form of calculus on the surface of teeth. Calculus is a solid material. It bonds to the surface of teeth over a period of time, and should be removed periodically to maintain healthy teeth.

Many devices and methods have been developed in attempts to better clean teeth. For example, U.S. Pat. No. 3,956,826 entitled "Ultrasonic Device and Method" issuing to Perdreaux, Jr. on May 18, 1976, discloses a hand held ultrasonic cleaning device used to clean teeth. Another device using a different technique is disclosed in U.S. Pat. No. 3,972,123 entitled "Air-Abrasive Prophylaxis Equipment" issuing to Black on Aug. 3, 1976. U.S. Pat. No. 3,972,123 discloses a device for directing an air-abrasive stream or jet at teeth for the purpose of cleaning the surface thereof with insoluble abrasive particles. A method of cleaning teeth is disclosed in U.S. Pat. No. 4,174,571 entitled "Method for Cleaning Teeth" issuing to Gallant on Nov. 20, 1979, which utilizes the device as disclosed in U.S. Pat. No. 3,972,123. The U.S. Pat. No. 4,174,571 discloses a method for cleaning teeth using an air-abrasive stream or jet with water soluble abrasive particles.

Additionally, it has been known to use ultrasonic dental handpieces in other dental applications. For example, U.S. Pat. No. 4,492,574 entitled "Ultrasonic Endodontic Dental Apparatus" issuing to Warrin et al on Jan. 8, 1985, discloses an ultrasonic dental handpiece for use in endodontics and root canal work, which is herein incorporated by reference.

While all of the above identified U.S. patents disclose apparatus and methods which adequately perform the functions for which they were intended, none of them disclose an apparatus and method for easily removing calculus from within the periodontal pocket. Therefore, there is a need for an improved apparatus and method for easily removing calculus from within the periodontal pocket.

SUMMARY OF THE INVENTION

The present invention relates to an apparatus and method for easily removing calculus from deep within the periodontal pocket. An ultrasonically driven handpiece has an abrasive tool attached thereto. The tool is relatively long and has a diameter small enough to be placed between a tooth and surrounding gum and bone. The vibrating abrasive tool easily removes the calculus deposits bonded to the tooth without unnecessarily traumatizing the surrounding gum and bone. Additionally, the diameter of the tool aids in the ability of the dentist to tactually sense the location of fine calculus deposits. A fluid spray is also used to aid in cooling and removal of loosened calculus.

Accordingly, it is an objective of the present invention to remove calculus easily and quickly.

It is an advantage of the present invention that removal of calculus is accomplished without unduly traumatizing surrounding bone and tissue.

It is a feature of the present invention that a specially sized diameter abrasive tool is used.

DETAIL DESCRIPTION OF THE PREFERRED EMBODIMENTS

Figure 1:
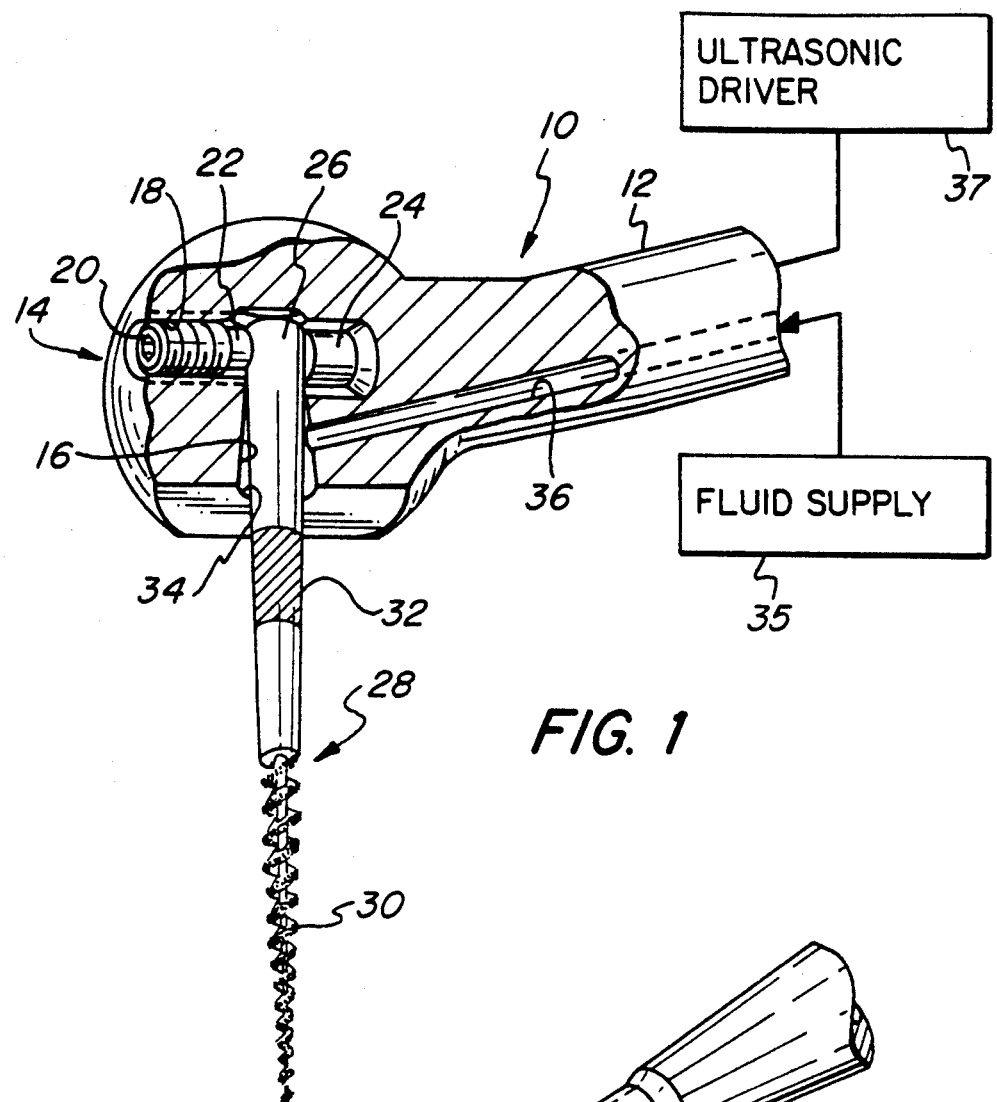
FIG. 1 is a perspective view illustrating a portion of one embodiment of the present invention.

FIG. 1 is a partial perspective view illustrating one embodiment of the present invention. A portion of an ultrasonic dental handpiece 10 is shown. The ultrasonic dental handpiece 10 may be a complete operable unit, or only a removable portion of a larger ultrasonic device, as is commonly used in other ultrasonic dental handpieces. For this reason only a portion of the handpiece 10 is illustrated. A handle 12 is attached to a head 14. Within head 14 is a tool bore 16. Additionally within head 14 is a threaded bore 18. Within threaded bore 18 is placed a screw 20. The screw 20 has a seat 22 at one end. A stop 24 is positioned opposite the threaded bore 18. A tool 28 is placed within the tool bore 16. The tool bore 16 has a diameter slightly larger than the diameter of the portion of tool 28 fitting therein. Tool 28 has a fixed end 26. The fixed end 26 is positioned between seat 22 and stop 24. The distal end of tool 28 has an abrasive portion 30. The abrasive portion 30, in FIG. 1, is illustrated as a file with ridged surfaces. Between the head 14 and abrasive portion 30, a reference or depth gauge surface 32 is placed on tool 28.

A fluid channel 36 is formed within handle 12 and head 14. One end of the fluid channel 36 is connected to a fluid supply illustrated by box 35, and the other end is open to tool bore 16. Because tool bore 16 is slightly larger than the diameter of tool 28, an annular aperture 34 is formed around the circumference of tool 28. Therefore, fluid is directed along the circumference of tool 28. The fluid is used to cool and wash away particles near the working end of tool 28. Coupled to the handle 12 and head portion 14 is an ultrasonic driver represented by box 37. The ultrasonic driver 37 is used to ultrasonically drive or vibrate the tool 28.

The tool 28 can be inserted and removed from the head 14 by loosening or tightening screw 20. When the tool 28 is inserted into the tool bore 16 such that the fixed end 26 is between the seat 22 and stop 24, the screw 20 is tightened securely fixing the tool 28 within the head 14. This permits the use of different size tools, or the replacement of worn or broken tools.

Figure 2:
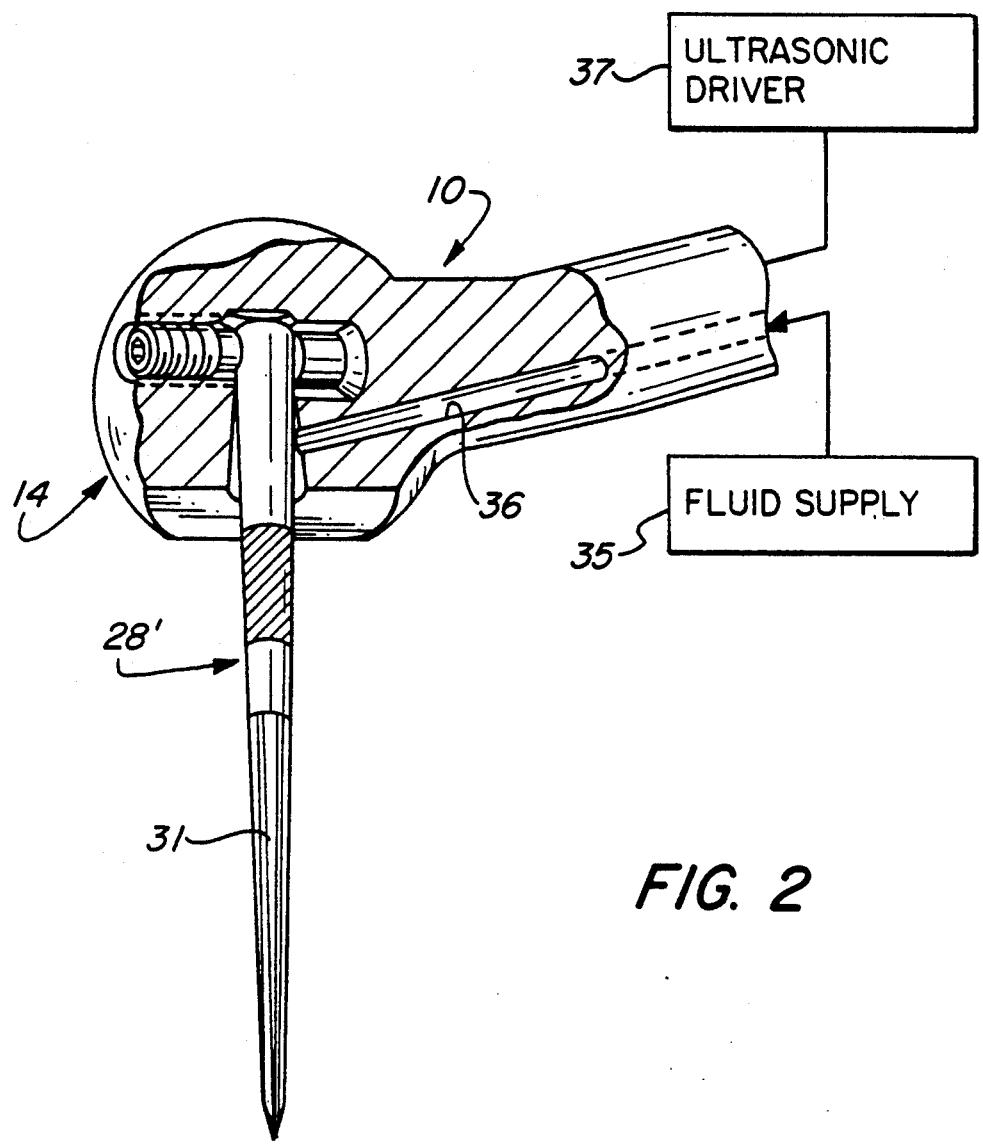
FIG. 2 is a perspective view illustrating another embodiment of the present invention.

FIG. 2 illustrates an embodiment of the invention similar to that illustrated in FIG. 1 with the exception that the tool 28 has an abrasive portion 31 with a diamond coating. The diamond coating 31 improves tactile feedback to the dentist. The improved tactile feedback permits locating and removing fine calculus deposits by the dentist.

Figure 3:
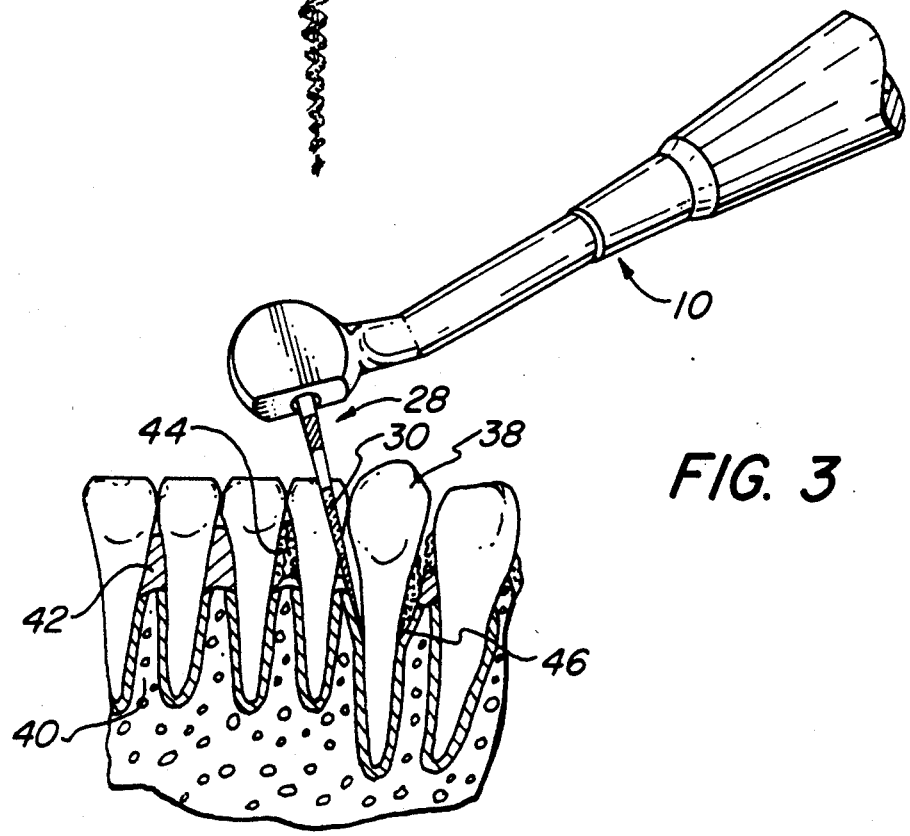
FIG. 3 is a representative illustration of the use of the invention illustrated in FIGS. 1 and 2.

FIG. 3 illustrates the method of removing calculus deposits from the surface of teeth with a device as illustrated in the embodiments of FIGS. 1 and 2. The dental handpiece 10 with the tool 28 attached is easily positioned adjacent a tooth 38. The tool 28 has a diameter along the length of the abrasive portion 30 that is sufficiently small to fit between the gingiva or gum 42 and the bone 40, forming the periodontal pocket 46 of the tooth 38, to remove the calculus 44. The maximum diameter of the abrasive portion 30 of tool 28 being 0.014 inches and the minimum diameter of the abrasive portion being 0.0065 inches therefore, tool 28 is conical. It has been discovered that anything larger than a diameter of 0.014 inches is too large to efficiently remove calculus from the tooth surface while providing minimal damage to the surrounding tissue and bone. The relatively small diameter of the tool 28, additionally results in the tool 28 being flexible.

Therefore, from the above, it should be clear that the present invention constitutes a significant advance in the dental art which provides an apparatus and method for removing calculus deposits from teeth easily and quickly and with efficiencies that heretofore have not been possible. Additionally, although the preferred embodiments have been illustrated and described, it will be obvious to those skilled in the art that various modifications may be made without departing from the spirit and scope of this invention.

What is claimed:

1. A dental handpiece for removing calculus from the surface of teeth below the gum line in the periodontal pocket comprising:
   a handle;
   a head attached to said handle having a tool bore;
   an elongated conically shaped abrasive tool having a working small diameter distal end and a larger diameter fixed end, the fixed end fitting within the tool bore, the working small diameter distal end extending from the tool bore and having a maximum diameter of less than 0.014 inches, the abrasive tool diameter at the point of exit from the tool bore being less than the diameter of the tool bore whereby an annular aperture is formed between the interior surface of the tool bore and the exterior surface of the abrasive tool at the point of exit from the tool bore;
   attachment means, associated with said head and said elongated conical shaped abrasive tool, for releasably attaching said elongated conical shaped abrasive tool to said head;
   depth reference indicia placed on said abrasive tool between the fixed end and the working small diameter distal end;
   fluid means, connected to the tool bore and the annular aperture, for providing cooling and irrigation fluid along the circumference of said abrasive tool; and
   ultrasonic drive means, coupled to said abrasive tool, for ultrasonically vibrating said tool,
   whereby calculus is removed without unnecessarily traumatizing bone and tissue surrounding the tooth.

2. A dental handpiece for removing calculus as in claim 1 wherein:
   said abrasive tool is a file having ridged surfaces.

3. A dental handpiece for removing calculus as in claim 1 wherein:
   said abrasive tool is diamond coated.

4. A dental handpiece for removing calculus from the surface of teeth below the gum line in the periodontal pocket comprising:
   a handle;
   a head attached to said handle having a tool bore and a threaded bore, the longitudinal axis of the tool bore being substantially perpendicular to the longitudinal axis of the threaded bore;
   an elongated conically shaped abrasive tool having a working small diameter distal end and a larger diameter fixed end, the fixed end fitting within the tool bore and extending to the threaded bore, the working small diameter distal end extending from the tool bore and having a maximum diameter of less than 0.014 inches, the abrasive tool diameter at the point of exit from the tool bore being less than the diameter of the tool bore whereby an annular aperture is formed between the interior surface of the tool bore and the exterior surface of the abrasive tool at the point of exit from the tool bore;
   a screw threaded into the threaded bore and contacting the fixed end of said abrasive tool securely holding said abrasive tool within the tool bore;
   depth reference indicia placed on said abrasive tool between the fixed end and the working small diameter distal end;
   fluid means, connected to the tool bore and the annular aperture, for providing cooling and irrigation fluid along the circumference of said abrasive tool; and
   ultrasonic drive means, coupled to said abrasive tool, for ultrasonically vibrating said tool,
   whereby calculus is removed without unnecessarily traumatizing bone and tissue surrounding the tooth.

* * * * *